US012747254B2

(12) United States Patent
Adam et al.

(10) Patent No.: US 12,747,254 B2
(45) Date of Patent: Sep. 29, 2026

(54) PROCESS FOR PREPARING HETEROCYCLIC PHARMACEUTICAL COMPOUNDS

(71) Applicant: Hoffmann-La Roche Inc., Little Falls, NJ (US)

(72) Inventors: Jean-Michel Adam, Rosenau (FR); Christophe Pfleger, Mulhouse (FR); Georg Wuitschik, Magden (CH)

(73) Assignee: Hoffmann-La Roche Inc., Branchburg, NJ (US)

( * ) Notice: Subject to any disclaimer, the term of this patent is extended or adjusted under 35 U.S.C. 154(b) by 437 days.

(21) Appl. No.: 18/369,140

(22) Filed: Sep. 15, 2023

(65) Prior Publication Data

US 2024/0182493 A1 Jun. 6, 2024

Related U.S. Application Data

(63) Continuation of application No. PCT/EP2022/056778, filed on Mar. 16, 2022.

(30) Foreign Application Priority Data

Mar. 18, 2021 (EP) .................................... 21163301

(51) Int. Cl.
*C07D 519/00* (2006.01)
*C07D 487/04* (2006.01)

(52) U.S. Cl.
CPC ......... *C07D 519/00* (2013.01); *C07D 487/04* (2013.01)

(58) Field of Classification Search
CPC ... C07D 519/00; C07D 487/04; A61K 31/519
See application file for complete search history.

(56) References Cited

U.S. PATENT DOCUMENTS

| | | | |
|---|---|---|---|
| 3,642,797 | A | 2/1972 | Lesher et al. |
| 10,882,868 | B2 | 1/2021 | Ranti et al. |
| 11,390,632 | B2 | 7/2022 | Adam et al. |
| 11,827,646 | B2 | 11/2023 | Ratni et al. |
| 2017/0197990 | A1 | 7/2017 | Ratni et al. |
| 2022/0324881 | A1 | 10/2022 | Adam et al. |

FOREIGN PATENT DOCUMENTS

| | | | |
|---|---|---|---|
| CN | 116997555 | A | 11/2023 |
| WO | 2004/072033 | A2 | 8/2004 |
| WO | 2013/130943 | A1 | 9/2013 |
| WO | 2015/173181 | A1 | 11/2015 |
| WO | 2019/057740 | A1 | 3/2019 |
| WO | 2020/079203 | A1 | 4/2020 |
| WO | 2022/194800 | A1 | 9/2022 |

OTHER PUBLICATIONS

Enamine LLC et al., CAS Registry Database, 2344679-41-8, (Imidazo [1,2-b] pyridazine-6-carboxylic acid, 2,8-dimethyl-C9H9N302), pp. 1; Creation Date Jun. 24, 2019.

"International Preliminary Report on Patentability—PCT/EP2022/056778" (Report Issuance Date: Sep. 12, 2023; Chapter I), :pp. 1-8 (Sep. 28, 2023).

"International Search Report—PCT/EP2022/056778" (w/Written Opinion), :pp. 1-17 (Mar. 9, 2023).

Moessner, C., et al. Complete Accounts of Integrated Drug Discovery and Development: Recent Examples from the Pharmaceutical Industry "Chapter 8: Development and Optimization of the Manufacturing Process for RNA-Splicing Modifier Risdiplam RG7916," Pesti, J. & Abdel-Magid, A., eds., Washington, D.C.—USA: American Chemical Society, vol. 1423:301-332 (Dec. 16, 2022).

Ratni, H., et al., "Discovery of Risdiplam, a Selective Survival of Motor Neuron-2 (SMN2) Gene Splicing Modifier for the Treatment of Spinal Muscular Atrophy (SMA)" J Med Chem 61(15):6501-6517 (Jul. 25, 2018).

*Primary Examiner* — Robert H Havlin

(57) ABSTRACT

The present invention relates to a process for the preparation of 7-(4.7-diazaspiro[2.5]octan-7-yl)-2-(2.8-dimethylimidazo[1.2-b]pyridazin-6-yl)pyrido[1.2-a]pyrimidin-4-one derivatives useful as pharmaceutically active compounds.

16 Claims, No Drawings

PROCESS FOR PREPARING HETEROCYCLIC PHARMACEUTICAL COMPOUNDS

CROSS-REFERENCE TO RELATED APPLICATIONS

This application is a continuation of International Application No. PCT/EP2022/056778 having an International filing date of Mar. 16, 2022, which claims benefit of priority to European Patent Application No. 21163301.1, filed Mar. 18, 2021, each of which is incorporated by reference in its entirety.

FIELD OF THE INVENTION

The present invention relates to a process for the preparation 7-(4,7-diazaspiro[2.5]octan-7-yl)-2-(2,8-dimethylimidazo[1,2-b]pyridazin-6-yl)pyrido[1,2-a]pyrimidin-4-one useful as pharmaceutically active compounds.

In a first aspect, the present invention provides a process for the preparation of a compound of formula (I) hydrates, solvates or the HCl salt thereof:

(I)

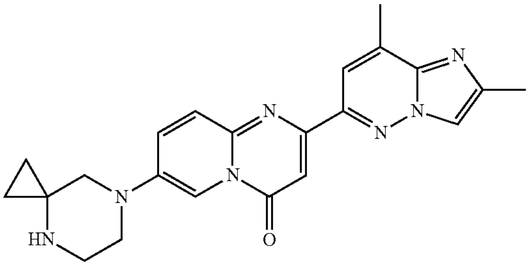

which comprises reacting compound of formula (II):

(II)

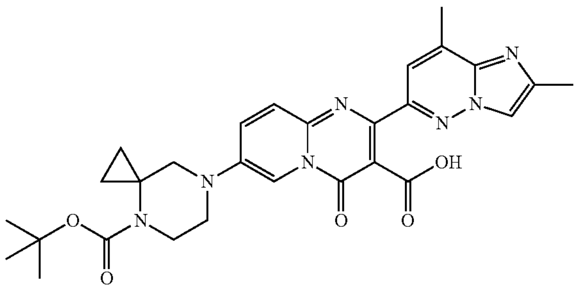

with a strong acid (to effect the decarboxylation and Boc-deprotection), in particular sulfuric acid, methanesulfonic acid, triflic acid or hydrochloric acid, in particular methanesulfonic acid, triflic acid and HCl, more particularly HCl, most particularly wherein HCl is made in situ with an alcohol and acetyl chloride.

The process according to the first embodiment, wherein the water free HCl is used. It can as well be made in situ with an alcohol and acetyl chloride, in particular, methanol, ethanol, n-propanol, isopropanol or n-butanol and acetyl chloride in particular n-propanol and acetyl chloride.

In a particular embodiment, after strong acid addition and reaction (to effect Boc deprotection and decarboxylation), the pH of the resulting acid solution of I is adjusted via base addition to isolate the free base.

In particular, the preparation of compound of formula (I) is being carried out in the presence of an alcoholic solvent such as methanol, ethanol, n-propanol, isopropanol or n-butanol, in particular n-propanol or isopropanol, more particularly n-propanol.

In a particular embodiment, the present invention provides a process as described herein, wherein 5 to 20 equivalents, more particularly 7 to 10 equivalents of HCl with respect to the theoretical amount of compound of formula (II) is used.

In another embodiment, the present invention provides a process as described above for the preparation of compound of formula (I), wherein the reaction is carried out at a temperature between 80° C. to 120° C., particularly between 85° C. to 100° C., more particularly between 85° C. and 95° C.

In another embodiment, the present invention provides a process as described herein, wherein HCl is made in situ with acetyl chloride in n-propanol at a temperature between 0-60° C., particularly between 0-40° C. during the addition of acetyl chloride then heated up to 60° C., more particularly between 10-20° C. during the addition of acetyl chloride then heated up to 60° C. at atmospheric pressure.

In another embodiment, the present invention provides a process as described herein wherein to reach a temperature higher than the boiling point would the solvent a pressurized reactor.

The compounds of formula (I) are valuable pharmaceutical compounds, in particular 7-(4,7-diazaspiro[2.5]octan-7-yl)-2-(2,8-dimethylimidazo[1,2-b]pyridazin-6-yl)pyrido[1,2-a]pyrimidin-4-one as described in WO2015173181.

Unless otherwise stated, the following terms used in the specification and claims have the meanings given below:

"($C_1$-$C_6$)alkyl" refers to a branched or straight hydrocarbon chain of one to six carbon atoms, such as methyl, ethyl, n-propyl, isopropyl, n-butyl, isobutyl, sec-butyl, t-butyl, pentyl and hexyl.

The term "($C_3$-$C_8$)cycloalkyl" denotes a saturated monovalent saturated monocyclic hydrocarbon group of 3 to 8 ring carbon atoms. Examples for monocyclic ($C_3$-$C_8$)cycloalkyl are cyclopropyl, cyclobutanyl, cyclopentyl, cyclohexyl or cycloheptyl.

"base" refers to a chemical compound that deprotonates another compound when reacted with it. Suitable bases for use in accordance with this disclosure include but are not limited to, e.g., tertiary amines and basic alkali metal salts. In some embodiments, the tertiary amines include triethylamine, tributylamine, N-methylmorpholine and diisopropylethylamine. In some embodiments, the basic alkali metal salts include, e.g., lithium carbonate ($Li_2CO_3$), sodium carbonate ($Na_2CO_3$), potassium carbonate ($K_2CO_3$), cesium carbonate ($Cs_2CO_3$), sodium bicarbonate ($NaHCO_3$), lithium, cesium, sodium and potassium hydroxide, sodium and potassium alkoxides including, but not limited to, sodium and potassium t-butoxide, npropoxide, i-propoxide, ethoxide, methoxide, and the like, sodium amide ($NaNH_2$), potassium amide ($KNH_2$), and the like.

"crystallization" and "recrystallization" may be used interchangeably; referring to a process wherein a chemical compound that is dissolved or suspended in a solvent system leads to a stable polymorph or crystalline form of a particular chemical compound. For example the crystallization steps can be done by forming a crystal with a solvent and an anti-solvent.

"strong acid" refers to an acid that dissociates completely in an aqueous solution with a pKa <−1.74. The strong acids include, but are not limited to: sulphuric acid ($H_2$ $SO_4$), hydrohalogenic acid (i.e. HX" wherein X" is I, Br, Cl or F), methanesulfonic acid, triflic acid, nitric acid ($HNO_3$), phosphoric acid ($H_3PO_4$) and combinations thereof. Particularly, the strong acid is hydrohalogenic acid, wherein X" is Br or Cl. Most particularly, the strong acid is HCl.

"Tertiary amine" refers to an amine of formula formula $R^aN(R^b)R^c$ wherein $R^a$, $R^b$ and $R^c$ independently are selected from ($C_1$-$C_6$)alkyl, ($C_3$-$C_8$)cycloalkyl or phenyl. Representative examples include, but are not limited to, triethylamine, tributylamine, di-ethyl-methylamine, dimethyl-ethylamine, N,N-Dimethylaniline, N-methylmorpholine and methylethylbutylamine. Preferably, the tertiary amine is chosen from tributylamine, tripropylamine or triethylamine, more preferably triethylamine or tributylamine. The most preferred tertiary amine is tributylamine.

"ambient conditions" or "Room Temperature" refers conditions as experienced in a standard laboratory, e.g. atmospheric pressure, under Ar or $N_2$, ambient temperature between 18° C. and 28° C.

In a particular embodiment of the first aspect, the present invention provides a process for the preparation of a compound of formula (I) hydrates, solvates or the HCl salt thereof:

(I)

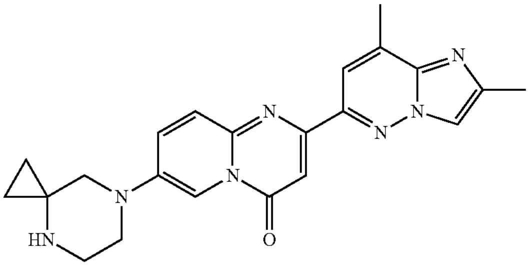

which comprises reacting compound of formula (II):

(II)

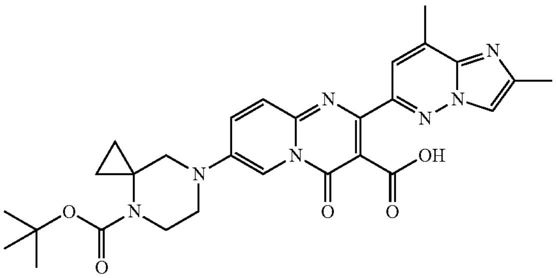

with HCl, most particularly wherein HCl is made in situ with an alcohol and acetyl chloride to obtain a compound of formula (IIa) or formula (IIb) which are then converted to a compound of formula (I)

(IIa)

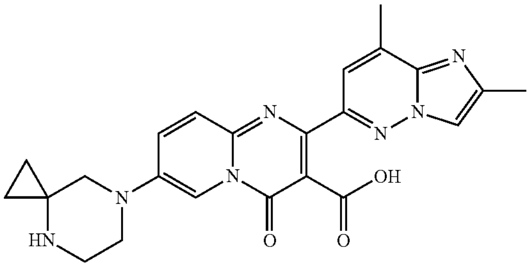

(IIb)

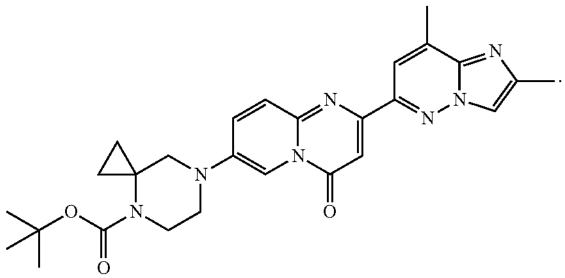

In another aspect (aspect 1'), the present invention provides a process for the preparation of a compound of formula (I) hydrates, solvates or the HCl salt thereof:

(I)

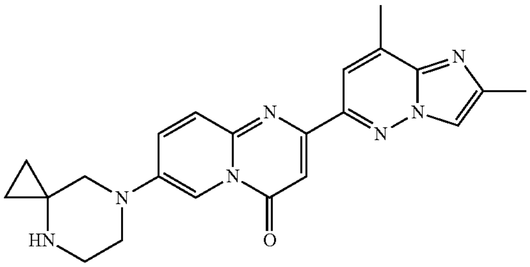

which comprises reacting compound of formula (IIa):

(IIa)

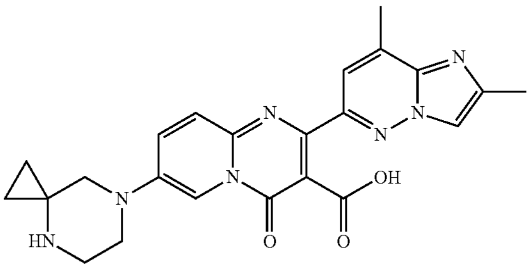

with HCl, most particularly wherein HCl is made in situ with an alcohol and acetyl chloride to obtain a compound of formula (I). In more particular embodiment, the present process may be heated.

In another aspect (aspect 2), the present invention provides a process for the preparation of a compound of formula (II):

(II)

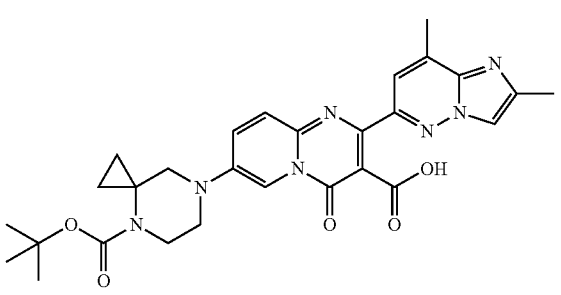

which comprises heating, in particular at a temperature above 70° C., in particular between 80° C. and 120° C., more particularly between 90° C. and 110° C., most particularly at 92° C.±5° C., a mixture of a compound of formula (III), (III)

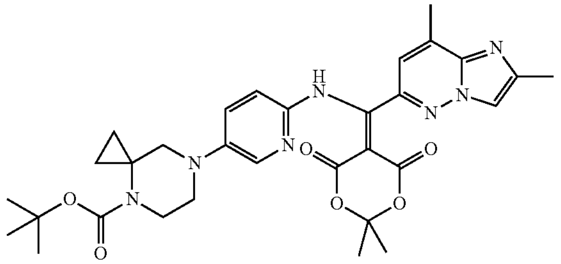

in particular in the presence of a solvent, more particularly wherein the solvent is selected from isopropanol, n-propanol, t-butanol, n-butamol, isobutanol, wherein the solvent is n-propanol or n-butanol or isopropanol, in particular n-propanol.

In a particular aspect 2, the present invention provides a process for the preparation of a compound of formula (II):

(II)

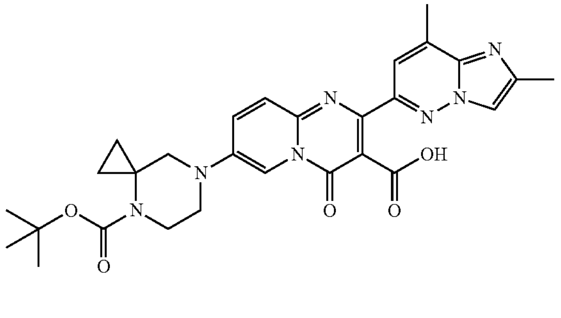

which comprises heating at 92° C.±5° C. a mixture of a compound of formula (III) in n-propanol.

(III)

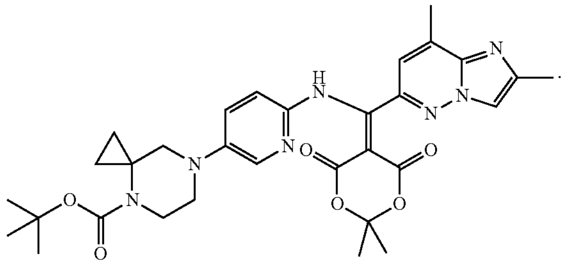

In yet another aspect (aspect 3), the present invention provides a process for the preparation of a compound of formula (III)

(III)

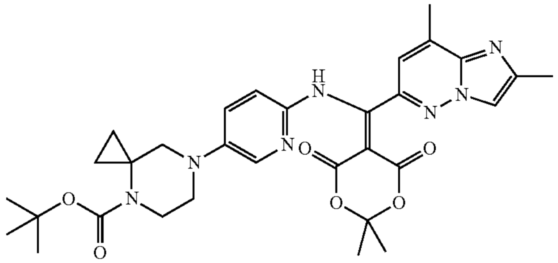

which comprises reacting a compound of formula (IV)

(IV)

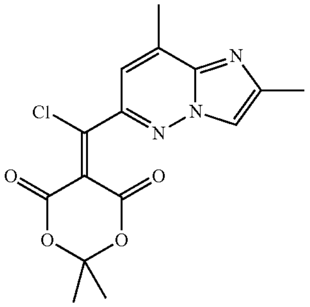

with a compound of formula (IVa):

(IVa)

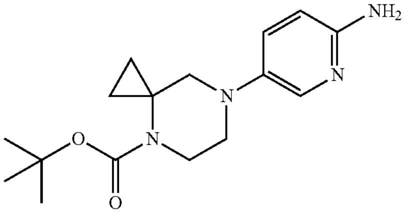

in particular in the presence of a tertiary amine, more particularly when the tertiary amine is selected from triethylamine, tripropylamine, diisopropylethylamine, tributiyamine, most particularly when the tertiary amine is tributylamine, in particular in the presence of a solvent, more particularly wherein the solvent is selected from dichloromethane, MeTHF, THF, most particularly wherein the solvent is dichloromethane.

The amount of compound of formula (IVa) is adjusted as to ensure efficient conversion of compound of formula (IV) to compound of formula (III) while avoiding unnecessary excess.

In a particular embodiment of aspect 3, the present invention provides a process as described herein, wherein 0.8 to 1.2 equivalents, more particularly 0.85 to 1, most particularly around 0.9 equivalents of a compound of formula (IVa) with respect to the theoretical amount of compound of formula (IV) is used. It is to be noted that the use of below stoichiometric amount, in particular 0.9 equivalent, of a compound of formula (Iva) with respect to the theoretical amount of compound of formula (IV) leads to the best yield and the least impurities.

In another embodiment of aspect 3, the present invention provides a process as described above for the preparation of compound of formula (III), wherein the reaction is carried out at a temperature between 0° C. to 40° C., particularly between 20° C. to 30° C., more particularly around 25° C.±5° C.

In yet another aspect (aspect 4), the present invention provides a process for the preparation of a compound of formula (IV)

(IV)

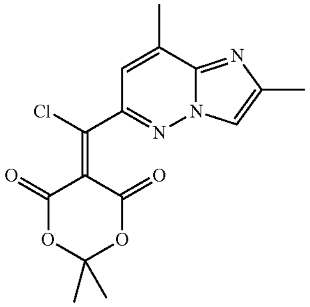

which comprises reacting a compound of formula (V) or its respective tautomer

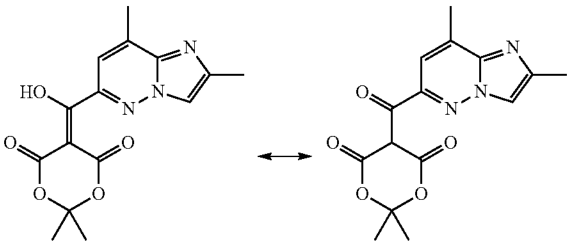

(V) (V-tautomer)

with oxalyl chloride, in particular in presence of a solvent, more particularly wherein the solvent is selected from dichloromethane, 2-MeTHF, THF, DMF, NMP, more particularly from 2-MeTHF and THF and dichloromethane most particularly wherein the solvent is dichloromethane.

In a particular embodiment of aspect 4, the present invention provides a process as described herein, wherein 0.9 to 1.4 equivalents, particularly 0.9 to 1.3 more particularly 0.9 to 1.2 equivalents of oxalyl chloride with respect to the theoretical amount of compound of formula (V) is used. In more particular embodiment, oxalyl chloride is titrated from 0.9 equivalent up to 1.2 to 1.3 equivalents with respect to the theoretical amount of compound of formula (V).

In a particular embodiment of aspect 4, the present invention provides a process as described herein, wherein oxalyl chloride chlorodehydrates the compound of formula (V) by following the conversion by HPLC.

In another embodiment of aspect 4, the present invention provides a process as described above for the preparation of compound of formula (IV), wherein the reaction is carried out at a temperature between 0° C. to 40° C., particularly between 15° C. to 30° C., more particularly at 20° C.±5° C.

In yet another aspect (aspect 5), the present invention provides a process for the preparation of a compound of formula (V)

(V)

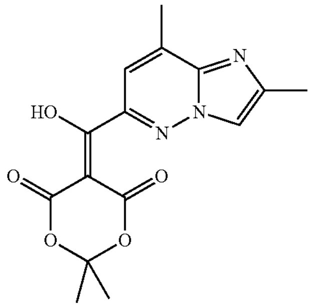

which comprises reacting a compound of formula (VI)

(VI)

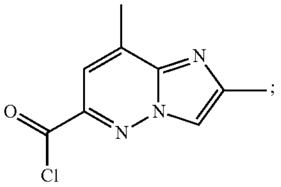

with 2,2-dimethyl-1,3-dioxane-4,6-dione, also known as Meldrum's acid, in particular in presence of a solvent, more particularly wherein the solvent is selected from dichloromethane, 2-MeTHF, THF, DMF, NMP, more particularly from 2-MeTHF and THF and dichloromethane most particularly wherein the solvent is dichloromethane.

In a particular embodiment of aspect 5, the present invention provides a process as described herein, wherein DMAP is present, more particularly wherein 2.5 to 5.0 equivalents, more particularly 3.0 to 4.0 equivalents, most preferably around 3.2 equivalent of DMAP with respect to the theoretical amount of compound of formula (VI). The DMAP amounts defined corresponds to the total amount present during the reaction and correspond to the sum of the amounts used during the acid chloride formation and the Meldrum's acid addition steps, when the process of aspect 5 is telescoped with process of aspect 6.

In a particular embodiment of aspect 5, wherein compound of formula VI is isolated, the present invention provides a process as described herein, wherein 2 to 2.5 equivalents, more particularly 2.2 to 2.4 equivalents, most preferably around 2.3 equivalent of 2,2-dimethyl-1,3-dioxane-4,6-dione with respect to the theoretical amount of compound of formula (VI) is used.

In another embodiment of aspect 5, the present invention provides a process as described above for the preparation of compound of formula (V), wherein the reaction is carried out at a temperature between 0° C. to 40° C., particularly between 15° C. to 30° C., more particularly at 20° C.±5° C.

In another embodiment, the present invention provides a process for the preparation of a compound of formula (V) as described above wherein aspects 5 and 6 are telescoped.

In yet another aspect (aspect 5'), the present invention provides a process for the preparation of a compound of formula (V)

(V)

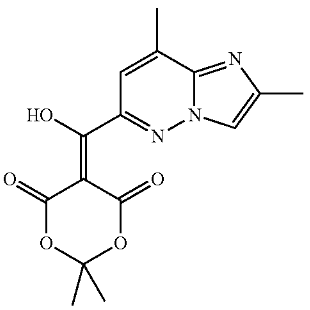

which comprises reacting a compound of formula (VII)

(VII)

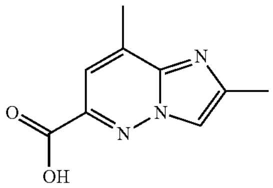

with oxalyl chloride, in particular in presence of a solvent, more particularly wherein the solvent is selected from dichloromethane, 2-MeTHF, THF, DMF, NMP, more particularly from 2-MeTHF and THF and dichloromethane most particularly wherein the solvent is dichloromethane followed by the addition of 2,2-dimethyl-1,3-dioxane-4,6-dione, also known as Meldrum's acid, wherein DMAP is present, more particularly wherein 2.5 to 5.0 equivalents, more particularly 3.0 to 4.0 equivalents, most preferably around 3.2 equivalent of DMAP are present with respect to the theoretical amount of compound of formula (VII).

In another embodiment of aspect 5', the present invention provides a process as described above for the preparation of compound of formula (V), wherein the reaction is carried out at a temperature between 0° C. to 40° C., particularly between 15° C. to 30° C., more particularly at 20° C.±5° C.

In yet another aspect (aspect 6), the present invention provides a process for the preparation of a compound of formula (VI)

(VI)

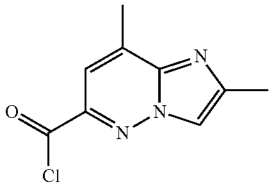

which comprises reacting a compound of formula (VII)

(VII)

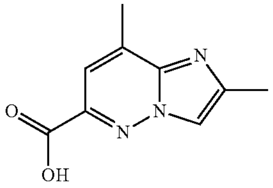

with oxalyl chloride, in particular in presence of a solvent, more particularly wherein the solvent is selected from dichloromethane, 2-MeTHF, THF, DMF, NMP, more particularly from 2-MeTHF and THF and dichloromethane most particularly wherein the solvent is dichloromethane.

In a particular embodiment of aspect 6, the present invention provides a process as described herein, wherein DMAP is present, more particularly wherein 1.5 to 4.0 equivalents, more particularly 2.0 to 3.0 equivalents, most preferably around 2.0 equivalent of DMAP with respect to the theoretical amount of compound of formula (VII).

It has been surprisingly found that the DMAP salt of compound of formula (VII) has increased solubility in dichloromethane compared to compound of formula (VII) which is advantageous with regards to mass transfer during the formation of the corresponding acid chloride.

In a particular embodiment of aspect 6, the present invention provides a process as described herein, wherein 1 to 1.1 equivalents, most particularly 1 equivalent of a oxalyl chloride with respect to compound of formula (VII) is used.

In a particular embodiment of aspect 6, the present invention provides a process as described herein, wherein DMF is being used in particular with 1.15 equivalent.

In another embodiment of aspect 6, the present invention provides a process as described above for the preparation of compound of formula (VI), wherein the reaction is carried out at a temperature between 10° C.±2° C. to 40° C.±2° C., particularly between 25° C.±2° C. to 40° C.±2° C., more particularly between 35° C.±2° C. and 40° C.±2° C.

In yet another aspect (aspect 7), the present invention provides a process for the preparation of a compound of formula (VII)

(VII)

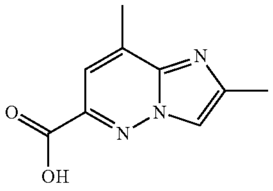

which comprises reacting a compound of formula (VIII)

(VIII)

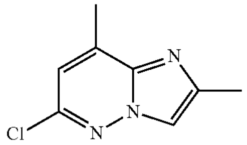

with carbon monoxide in the presence of a catalyst (such as $Pd(PPh_3)_4$, $Pd(PPh_3)_2Cl_2$, $PdCl_2(dppf)$, $PdCl_2(dppf)\cdot CH_2Cl_2$, $PdCl_2(dppp)$, in particular in the presence of $PdCl_2(dppf)$) and in the presence of a base, particularly a tertiary amine, acetonitrile and in presence of water and a solvent, more particularly wherein the solvent is selected from MeOH, EtOH, iPrOH, AmOH, n-PrOH, DMF, DMA, Toluene, THF or 2-Me-THF, most particularly wherein the solvent is acetonitrile and water.

In a particular embodiment of aspect 7, the present invention provides a process as described herein, wherein 1 to 150 bar, particularly 20 to 70 bar, most particularly 50 to 70 bar of carbon monoxide with respect to compound of formula (VIII) is used.

In a particular embodiment of aspect 7, the present invention provides a process as described herein, wherein 0.01 mol % to 10 mol %; more particularly 0.1 mol % to 2 mol %, most particularly 0.5 mol % to 1.5 mol %. of the catalyst with respect to compound of formula (VIII) is used.

In a particular embodiment of aspect 7, the present invention provides a process as described herein, wherein 0.1 to 10 equivalents, more particularly 1.5 to 2.5 equivalents of tertiary amine with respect to compound of formula (VIII) is used.

In another embodiment of aspect 7, the present invention provides a process as described above for the preparation of compound of formula (VII), wherein the reaction is carried out at a temperature between 20° C.±2° C. to 150° C.±2° C., particularly between 60° C.±2° C. to 110° C.±2° C., more particularly between 80° C.±2° C. and 100° C.±2° C.

In yet another aspect (aspect 8), the present invention provides a process for the preparation of a compound of formula (VIII)

(VIII)

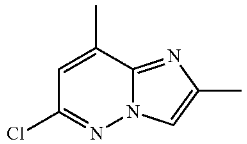

which comprises:

a) Reacting a compound of formula (X)

(X)

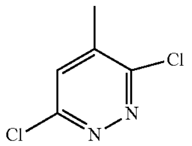

with $NH_4OH$ to obtain compounds of formulae (IXa) and (IXb);

b) reacting compounds of formulae (IXa) and (IXb)

(IXa)

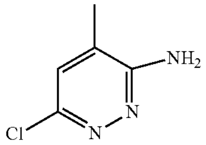

(IXb)

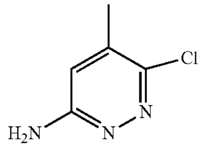

with 1-bromo-2,2-dimethoxypropane, in the presence of pyridinium p-toluenesulfonate, to obtain a compound of formula (VIII). Step b) is optionally followed by at least a purification step, in particular wherein a purification step is an inverse crystallization. The inverse crystallization is optionally followed by a chromatography purification.

In yet another aspect (aspect 8'), the present invention provides a process for the preparation of a compound of formula (VIII)

(VIII)

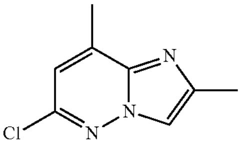

which comprises:

a) Reacting a compound of formula (X)

(X)

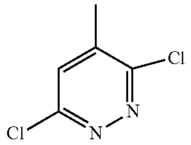

with $NH_4OH$ to obtain compounds of formula (IXa);

b) reacting compounds of formula (IXa)

(IXa)

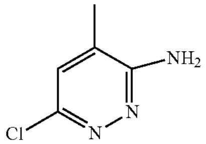

with 1-bromo-2,2-dimethoxypropane, in the presence of pyridinium p-toluenesulfonate, to obtain a compound of formula (VIII). Step b) is optionally followed by at least a purification step, in particular wherein a purification step is an inverse crystallization. The inverse crystallization is optionally followed by a chromatography purification.

Alternatively, compound of formula (VIII) can be prepared in accordance with the process described in WO2015173181 and the process described in WO2019057740.

Compared to the process described in WO2015173181, the purity of the crude compound of formula (VIII) can be enhanced by inverse crystallization, removing most of the undesired regioisomer arising from compound of formula (IXb), to facilitate the final chromatographic purification In a particular embodiment, the present invention provides the process herein described according to aspect 8 wherein steps a) and b) are telescoped.

Compound of formula (IVa) can be prepared in accordance to the following steps:

(IVa)

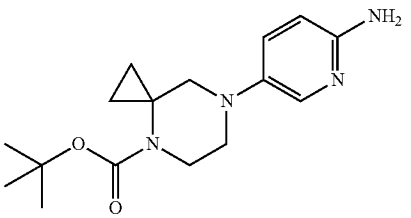

which comprises reacting a compound of formula (IVb)

(IVb)

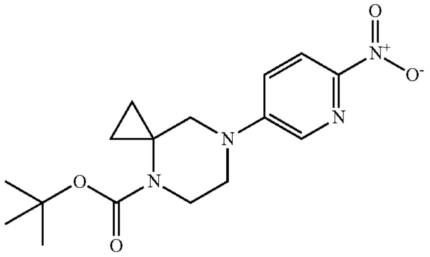

with a hetereogeneous transition metal hydrogenation catalyst, in particular wherein the hetereogeneous transition metal hydrogenation catalyst is Raney catalyst (e.g. Ra—Ni, Ra—Co,) Pd/C, $Pd(OH)_2/C$, $Pd/Al_2O_3$, $Au/TiO_2$, Rh/C, $Ru/Al_2O_3$, $Ir/CaCO_3$, Pt—V/C or Pt/C or combination thereof, in particular Pt—V/C, more particularly Pt 1% and V 2% on activated carbon. In particular, for the preparation of compounds of formulae (IVa), the reaction is carried out at a temperature between 0° C.±2° C. to 150° C.±2° C., particularly between 15° C.±2° C. to 70° C.±2° C., more particularly between 20° C.±2° C. and 35° C.=2° C.

Compound of formula (IVb) can be also prepared in accordance to scheme 1.

Scheme 1

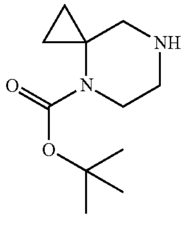

(IVd)

+

-continued

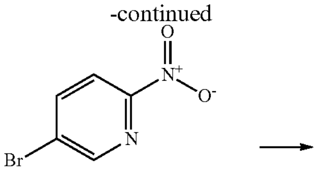

(IVc)

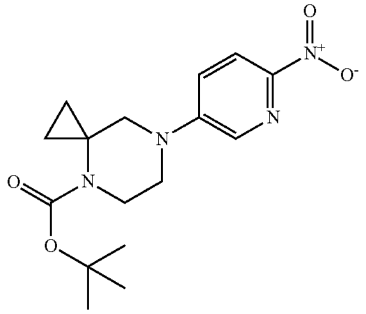

(IVb)

Compound of formula (IVa and IVb) can be prepared by processes described in WO2019057740.

In another embodiment (aspect 9), the present invention provides a process for the preparation of a compound of formula (I) or the HCl salt thereof:

(I)

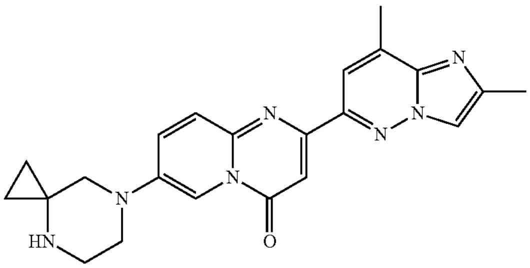

which comprises a) heating, in particular at a temperature above 70° C., in particular between 80° C. and 120° C., more particularly between 90° C. and 110° C., most particularly at 92° C.±5° C., a mixture of a compound of formula (III)

(III)

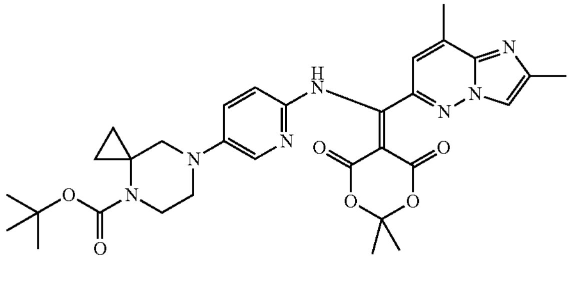

in particular in the presence of a solvent, more particularly wherein the solvent is selected from isopropanol, n-propanol, t-butanol, n-butamol, isobutanol, wherein the solvent is n-propanol or n-butanol or isopropanol, in particular n-propanol as previously described to obtain a compound of formula (II)

(II)

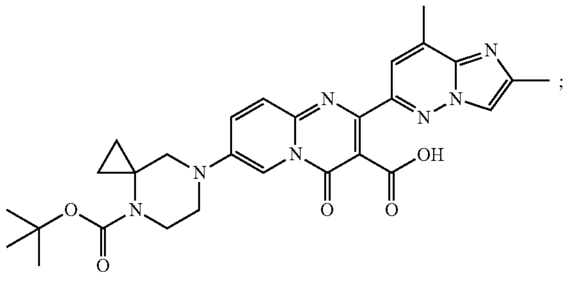

b) reacting compound of formula (II) with a strong acid (to effect the decarboxylation), in particular sulfuric acid, methanesulfonic acid, triflic acid or hydrochloric acid, in particular methanesulfonic acid, triflic acid and HCl, more particularly HCl, most particularly wherein HCl is made in situ with an alcohol and acetyl chloride as previously described to obtain a compound of formula (I).

In another embodiment (aspect 10), the present invention provides a process for the preparation of a compound of formula (I) or the HCl salt thereof:

(I)

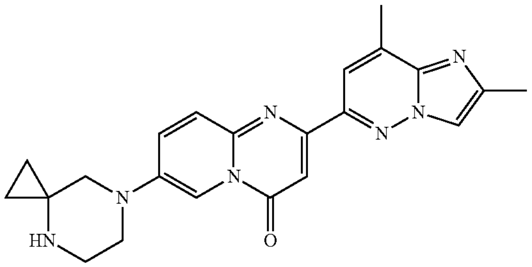

which comprises a) reacting a compound of formula (IV)

(IV)

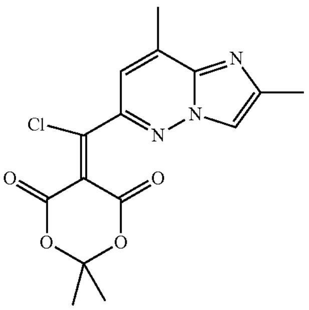

with a compound of formula (IVa):

(IVa)

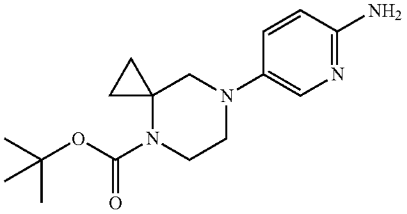

in particular in the presence of a tertiary amine, more particularly when the tertiary amine is selected from triethylamine, tripropylamine, diisopropylethylamine, tributlyamine, most particularly when the tertiary amine is tributylamine, in particular in the presence of a solvent, more particularly wherein the solvent is selected from dichloromethane, MeTHF, THF, most particularly wherein the solvent is dichloromethaneas previously described, to obtain a compound of formula (III)

(III)

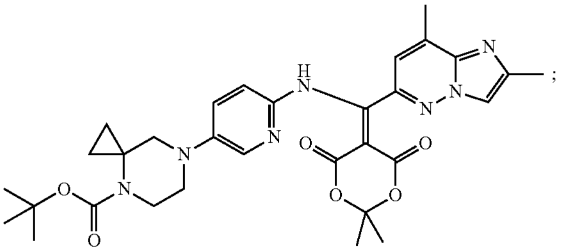

b) heating, in particular at a temperature above 70° C., in particular between 80° C. and 120° C., more particularly between 90° C. and 110° C., most particularly at 92° C.±5° C., a mixture of a compound of formula (III) in particular in the presence of a solvent, more particularly wherein the solvent is selected from isopropanol, n-propanol, t-butanol, n-butanol, isobutanol, wherein the solvent is n-propanol or n-butanol or isopropanol, in particular n-propanolas previously described to obtain a compound of formula (II)

(II)

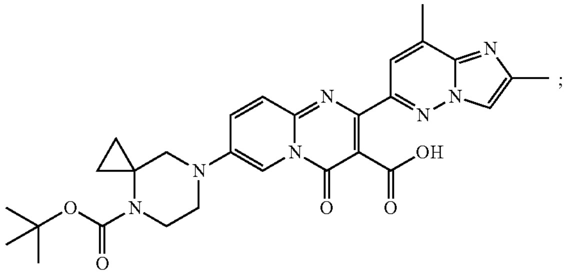

c) reacting compound of formula (II) with a strong acid (to effect the decarboxylation), in particular sulfuric acid, methanesulfonic acid, triflic acid or hydrochloric acid, in particular methanesulfonic acid, triflic acid and HCl, more particularly HCl, most particularly wherein HCl is made in situ with an alcohol and acetyl chloride as previously described to obtain a compound of formula (I).

In another embodiment (aspect 11), the present invention provides a process for the preparation of a compound of formula (I) or the HCl salt thereof:

(I)

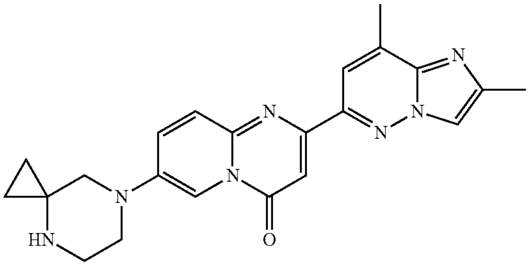

which comprises a) reacting a compound of formula (V) or its tautomer (V)

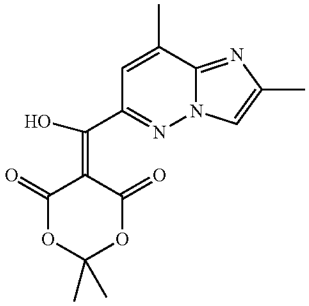

(V-tautomer)

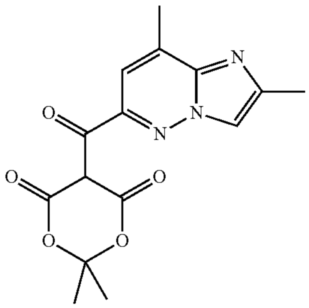

with oxalyl chloride, in particular in presence of a solvent, more particularly wherein the solvent is selected from dichloromethane, 2-MeTHF, THF, DMF, NMP, more particularly from 2-MeTHF and THF and dichloromethane most particularly wherein the solvent is dichloromethaneas previously described, to obtain a compound of formula (IV)

(IV)

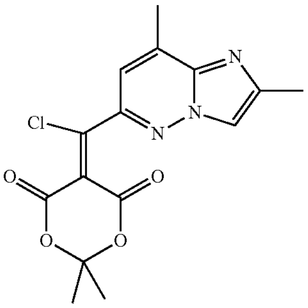

b) reacting a compound of formula (IV) with a compound of formula (IVa):

(IVa)

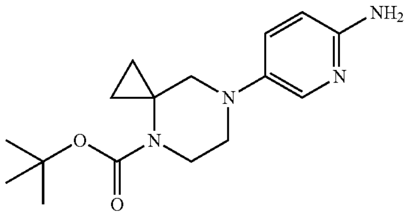

in particular in the presence of a tertiary amine, more particularly when the tertiary amine is selected from triethylamine, tripropylamine, diisopropylethylamine, tributlyamine, most particularly when the tertiary amine is tributylamine, in particular in the presence of a solvent, more particularly wherein the solvent is selected from dichloromethane, MeTHF, THF, most particularly wherein the solvent is dichloromethaneas previously described, to obtain a compound of formula (III)

(III)

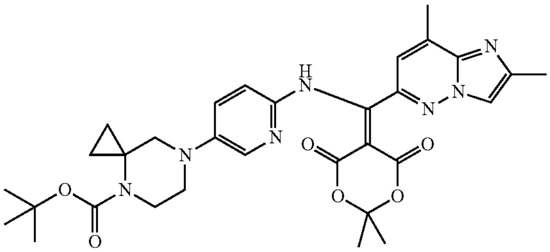

;

c) heating, in particular in particular at a temperature above 70° C., in particular between 80° C. and 120° C., more particularly between 90° C. and 110° C., most particularly at 92° C.±5° C., a mixture of a compound of formula (III) in a solvent, in particular in the presence of a solvent, more particularly wherein the solvent is selected from isopropanol, n-propanol, t-butanol, n-butanol, isobutanol, wherein the solvent is n-propanol or n-butanol or isopropanol, in particular n-propanol as previously described to obtain a compound of formula (II)

(II)

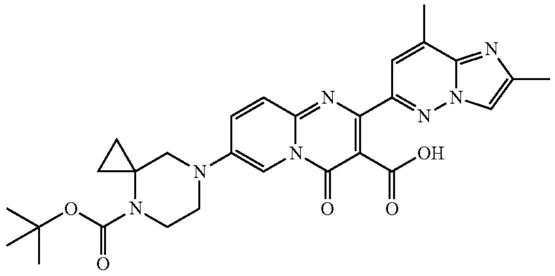

;

d) reacting compound of formula (II) with a strong acid (to effect the decarboxylation), in particular sulfuric acid, methanesulfonic acid, triflic acid or hydrochloric acid, in particular methanesulfonic acid, triflic acid and HCl, more particularly HCl, most particularly wherein HCl is made in situ with an alcohol and acetyl chloride as previously described to obtain a compound of formula (I).

In another embodiment (aspect 12), the present invention provides a process for the preparation of a compound of formula (I) or the HCl salt thereof:

(I)

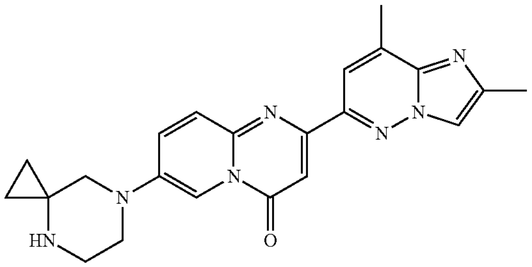

which comprises a) reacting a compound of formula (VI)

(VI)

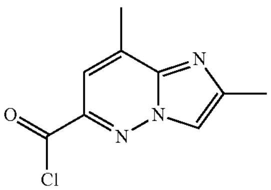

with 2,2-dimethyl-1,3-dioxane-4,6-dione, also known as Meldrum's acid, in particular in presence of a solvent, more particularly wherein the solvent is selected from dichloromethane, 2-MeTHF, THF, DMF, NMP, more particularly from 2-MeTHF and THF and dichloromethane most particularly wherein the solvent is dichloromethane, as previously described, to obtain a compound of formula (V) or its tautomer (V)

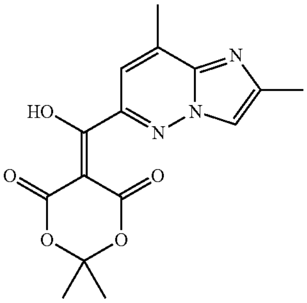

(V-tautomer)

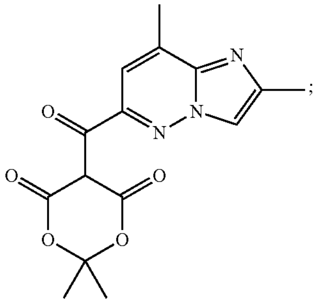

;

b) reacting a compound of formula (V) or its tautomer with oxalyl chloride, in particular in presence of a solvent, more particularly wherein the solvent is selected from dichloromethane, 2-MeTHF, THF, DMF, NMP, more particularly from 2-MeTHF and THF and dichloromethane most particularly wherein the solvent is dichloromethane as previously described, to obtain a compound of formula (IV)

(IV)

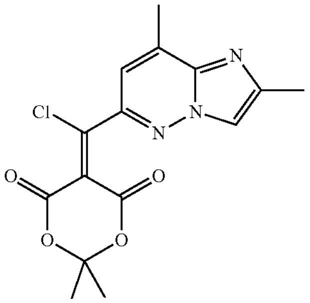

c) reacting a compound of formula (IV) with a compound of formula (IVa):

(IVa)

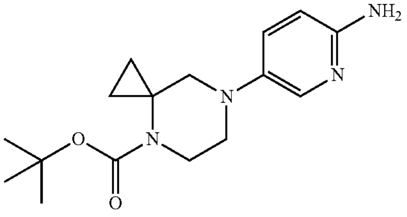

in particular in the presence of a tertiary amine, more particularly when the tertiary amine is selected from triethylamine, tripropylamine, diisopropylethylamine, tributlyamine, most particularly when the tertiary amine is tributylamine, in particular in the presence of a solvent, more particularly wherein the solvent is selected from dichloromethane, MeTHF, THF, most particularly wherein the solvent is dichloromethaneas previously described, to obtain a compound of formula (III)

(III)

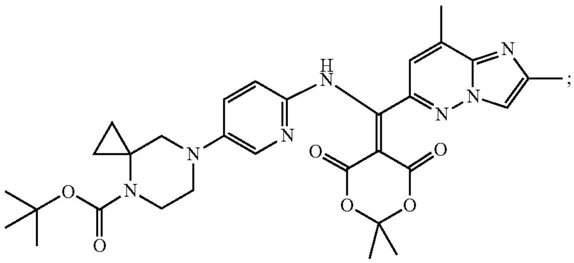
;

d) heating, in particular at a temperature above 70° C., in particular between 80° C. and 120° C., more particularly between 90° C. and 110° C., most particularly at 92° C.±5° C., a mixture of a compound of formula (III) in particular in the presence of a solvent, more particularly wherein the solvent is selected from isopropanol, n-propanol, t-butanol, n-butanol, isobutanol, wherein the solvent is n-propanol or n-butanol or isopropanol, in particular n-propanol as previously described to obtain a compound of formula (II)

(II)

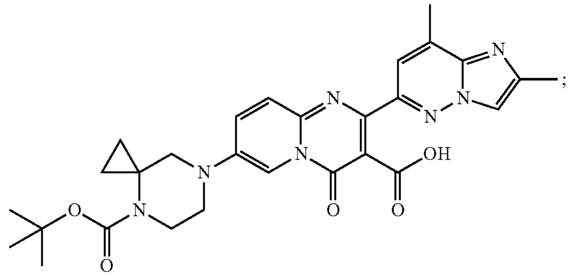
;

e) reacting compound of formula (II) with a strong acid (to effect the decarboxylation), in particular sulfuric acid, methanesulfonic acid, triflic acid or hydrochloric acid, in particular methanesulfonic acid, triflic acid and HCl, more particularly HCl, most particularly wherein HCl is made in situ with an alcohol and acetyl chloride 1, as previously described to obtain a compound of formula (I).

In another embodiment (aspect 13), the present invention provides a process for the preparation of a compound of formula (I) or the HCl salt thereof:

(I)

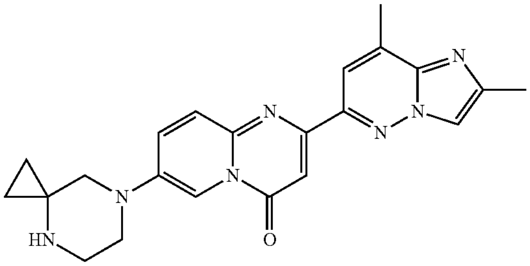

which comprises a) reacting a compound of formula (VII)

(VII)

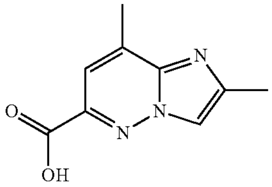

with oxalyl chloride, in particular in presence of a solvent, more particularly wherein the solvent is selected from dichloromethane, 2-MeTHF, THF, DMF, NMP, more particularly from 2-MeTHF and THF and dichloromethane most particularly wherein the solvent is dichloromethaneas previously described, to obtain a compound of formula (VI)

(VI)

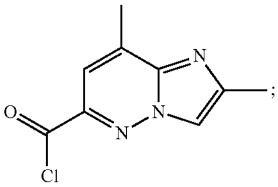
;

b) reacting a compound of formula (VI) with 2,2-dimethyl-1,3-dioxane-4,6-dione, also known as Meldrum's acid, in particular in presence of a solvent, more particularly wherein the solvent is selected from dichloromethane, 2-MeTHF, THF, DMF, NMP, more particularly from 2-MeTHF and THF and dichloromethane most particularly wherein the solvent is dichloromethane as previously described, to obtain a compound of formula (V) or its tautomer (V)

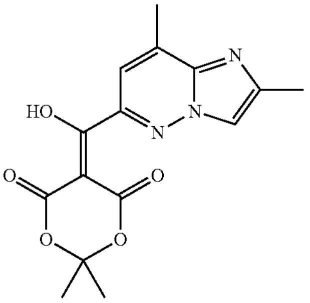

(V-tautomer)

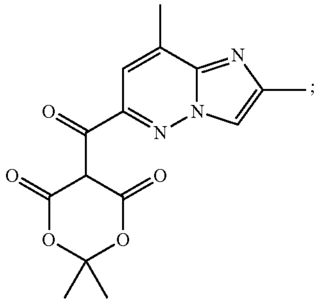

c) reacting a compound of formula (V) or its tautomer with oxalyl chloride in particular in presence of a solvent, more particularly wherein the solvent is selected from dichloromethane, 2-MeTHF, THF, DMF, NMP, more particularly from 2-MeTHF and THF and dichloromethane most particularly wherein the solvent is dichloromethane as previously described, to obtain a compound of formula (IV)

(IV)

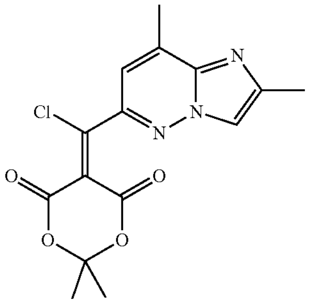

d) reacting a compound of formula (IV) with a compound of formula (IVa):

(IVa)

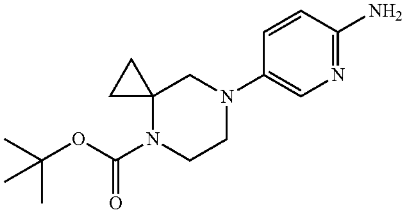

in particular in the presence of a tertiary amine, more particularly when the tertiary amine is selected from triethylamine, tripropylamine, diisopropylethylamine, tributlyamine, most particularly when the tertiary amine is tributylamine, in particular in the presence of a solvent, more particularly wherein the solvent is selected from dichloromethane, MeTHF, THF, most particularly wherein the solvent is dichloromethane as previously described, to obtain a compound of formula (III)

(III)

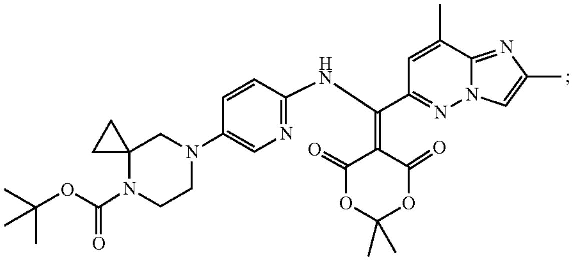

e) heating, in particular at a temperature above 70° C., in particular between 80° C. and 120° C., more particularly between 90° C. and 110° C., most particularly at 92° C.±5° C., a mixture of a compound of formula (III) in particular in the presence of a solvent, more particularly wherein the solvent is selected from isopropanol, n-propanol, t-butanol, n-butanol, isobutanol, wherein the solvent is n-propanol or n-butanol or isopropanol, in particular n-propanol as previously described to obtain a compound of formula (II)

(II)

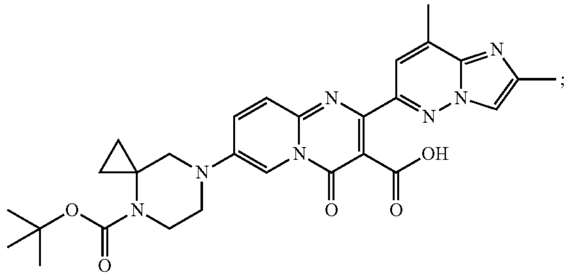

f) reacting compound of formula (II) with a strong acid (to effect the decarboxylation), in particular sulfuric acid, methanesulfonic acid, triflic acid or hydrochloric acid, in particular methanesulfonic acid, triflic acid and HCl, more particularly HCl, most particularly wherein HCl is made in situ with an alcohol and acetyl chloride as previously described to obtain a compound of formula (I).

In another embodiment (aspect 14), the present invention provides a process for the preparation of a compound of formula (I) or the HCl salt thereof:

(I)

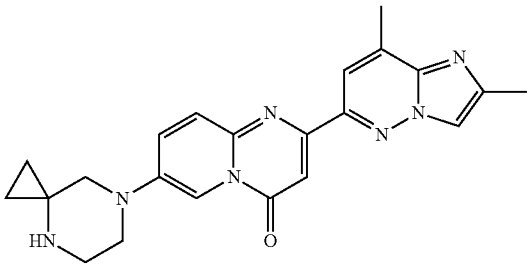

which comprises a) reacting a compound of formula (VIII)

(VIII)

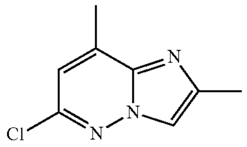

with carbon monoxide in the presence of a catalyst (such as $Pd(PPh_3)_4$, $Pd(PPh_3)_2Cl_2$, $PdCl_2(dppf)$, $PdCl_2(dppf)\cdot CH_2Cl_2$, $PdCl_2(dppp)$, in particular in the presence of $PdCl_2(dppf)$) and in the presence of a base, particularly a tertiary amine, acetonitrile and in presence of waterand a solvent, more particularly wherein the solvent is selected from MeOH, EtOH, iPrOH, AmOH, n-PrOH, DMF, DMA, Toluene, THF or 2-Me-THF, most particularly wherein the solvent is acetonitrile and water, as previously described, to obtain a compound of formula (VII)

(VII)

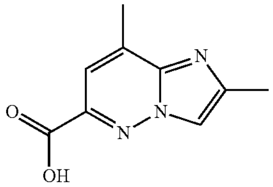

b) reacting a compound of formula (VII)

with oxalyl chloride, in particular in presence of a solvent, more particularly wherein the solvent is selected from dichloromethane, 2-MeTHF, THF, DMF, NMP, more particularly from 2-MeTHF and THF and dichloromethane most particularly wherein the solvent is dichloromethaneas previously described, to obtain a compound of formula (VI)

(VI)

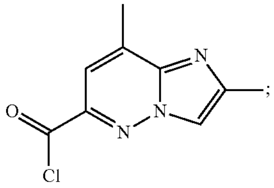

c) reacting a compound of formula (VI) with 2,2-dimethyl-1,3-dioxane-4,6-dione, also known as Meldrum's acid, in particular in presence of a solvent, more particularly wherein the solvent is selected from dichloromethane, 2-MeTHF, THF, DMF, NMP, more particularly from 2-MeTHF and THF and dichloromethane most particularly wherein the solvent is dichloromethane as previously described, to obtain a compound of formula (V) or its tautomer (V)

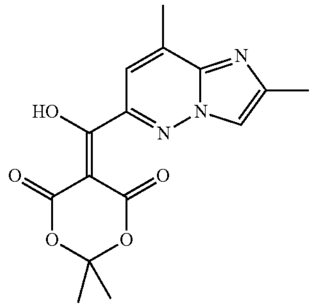

(V-tautomer)

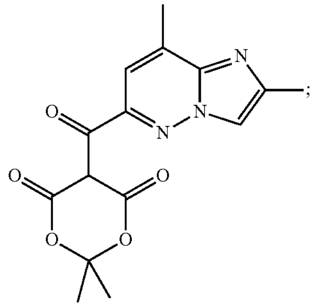

d) reacting a compound of formula (V) or its tautomer with oxalyl chloride in particular in presence of a solvent, more particularly wherein the solvent is selected from dichloromethane, 2-MeTHF, THF, DMF, NMP, more particularly from 2-MeTHF and THF and dichloromethane most particularly wherein the solvent is dichloromethaneas previously described, to obtain a compound of formula (IV)

(IV)

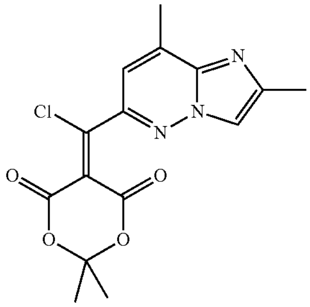

e) reacting a compound of formula (IV) with a compound of formula (IVa):

(IVa)

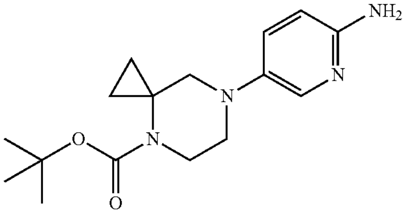

in particular in the presence of a tertiary amine, more particularly when the tertiary amine is selected from triethylamine, tripropylamine, diisopropylethylamine, tributlyamine, most particularly when the tertiary amine is tributylamine, in particular in the presence of a solvent, more particularly wherein the solvent is selected from dichloromethane, MeTHF, THF, most particularly wherein the solvent is dichloromethaneas previously described, to obtain a compound of formula (III)

(III)

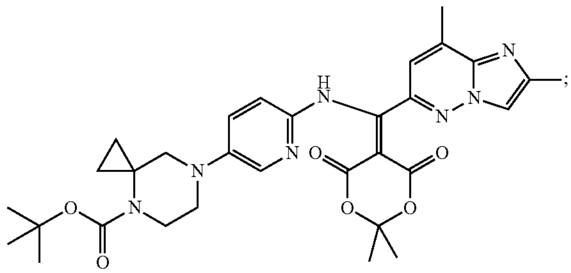

f) heating, in particular at a temperature above 70° C., in particular between 80° C. and 120° C., more particularly between 90° C. and 110° C., most particularly at 92° C.±5° C., a mixture of a compound of formula (III) in particular in the presence of a solvent, more particularly wherein the solvent is selected from isopropanol, n-propanol, t-butanol, n-butanol, isobutanol, wherein the solvent is n-propanol or n-butanol or isopropanol, in particular n-propanolas previously described to obtain a compound of formula (II)

(II)

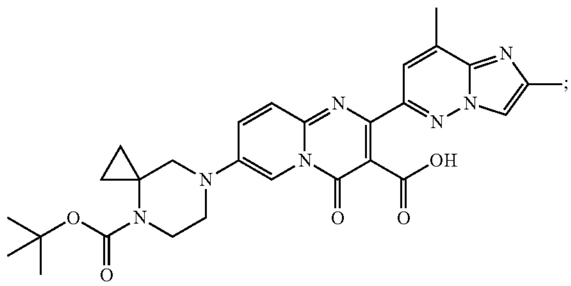

g) reacting compound of formula (II) with a strong acid (to effect the decarboxylation), in particular sulfuric acid, methanesulfonic acid, triflic acid or hydrochloric acid, in particular methanesulfonic acid, triflic acid and HCl, more particularly HCl, most particularly wherein HCl is made in situ with an alcohol and acetyl chloride as previously described to obtain a compound of formula (I).

In another embodiment (aspect 15), the present invention provides a process for the preparation of a compound of formula (I) or the HCl salt thereof:

(I)

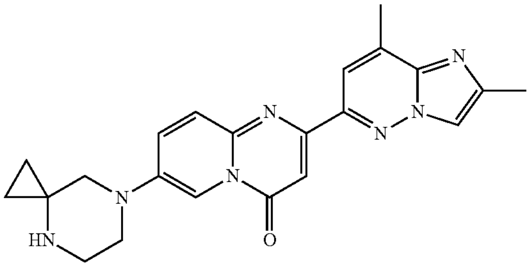

which comprises a) reacting a compound of formula (X)

(X)

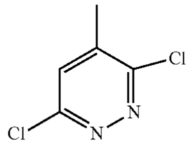

with $NH_4OH$ to obtain compounds of formulae (IXa) and (IXb)

(IXa)

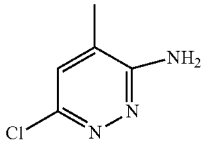

(IXb)

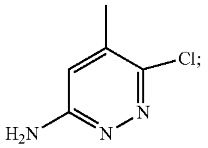

b) reacting compounds of formulae (IXa) and (IXb) with 1-bromo-2,2-dimethoxypropane, in the presence of pyridinium p-toluenesulfonate, to obtain a compound of formula (VIII)

(VIII)

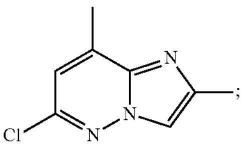

c) reacting a compound of formula (VIII) with carbon monoxide in the presence of a catalyst (such as $Pd(PPh_3)_4$, $Pd(PPh_3)_2Cl_2$, $PdCl_2(dppf)$, $PdCl_2(dppf)$ ·$CH_2Cl_2$, $PdCl_2$(dppp), in particular in the presence of $PdCl_2$(dppf)) and in the presence of a base, particularly a tertiary amine, acetonitrile and in presence of water and a solvent, more particularly wherein the solvent is selected from MeOH, EtOH, iPrOH, AmOH, n-PrOH, DMF, DMA, Toluene, THF or 2-Me-THF, most particularly wherein the solvent is acetonitrile and water as previously described, to obtain a compound of formula (VII)

(VII)

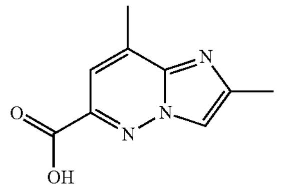

d) reacting a compound of formula (VII)

with oxalyl chloride, in particular in presence of a solvent, more particularly wherein the solvent is selected from dichloromethane, 2-MeTHF, THF, DMF, NMP, more particularly from 2-MeTHF and THF and dichloromethane most particularly wherein the solvent is dichloromethaneas previously described, to obtain a compound of formula (VI)

(VI)

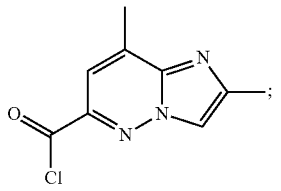

e) reacting a compound of formula (VI) with 2,2-dimethyl-1,3-dioxane-4,6-dione, also known as Meldrum's acid, in particular in presence of a solvent, more particularly wherein the solvent is selected from dichloromethane, 2-MeTHF, THF, DMF, NMP, more particularly from 2-MeTHF and THF and dichloromethane most particularly wherein the solvent is dichloromethane as previously described, to obtain a compound of formula (V) or its tautomer (V)

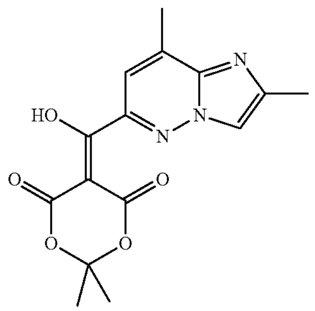

-continued (V-tautomer)

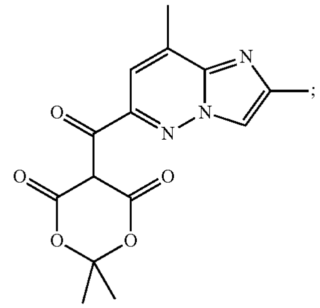

f) reacting a compound of formula (V) or its tautomer with oxalyl chloride in particular in presence of a solvent, more particularly wherein the solvent is selected from dichloromethane, 2-MeTHF, THF, DMF, NMP, more particularly from 2-MeTHF and THF and dichloromethane most particularly wherein the solvent is dichloromethane, in particular as previously described, to obtain a compound of formula (IV)

(IV)

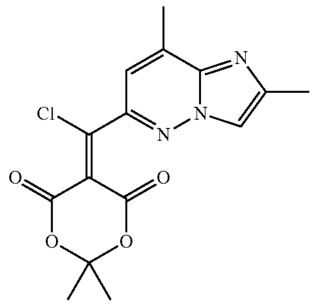

g) reacting a compound of formula (IV) with a compound of formula (IVa):

(IVa)

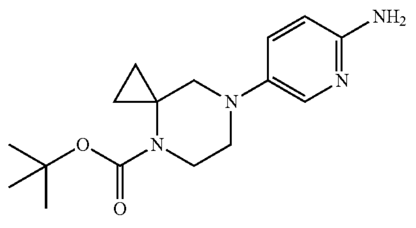

in particular in the presence of a tertiary amine, more particularly when the tertiary amine is selected from triethylamine, tripropylamine, diisopropylethylamine, tributlyamine, most particularly when the tertiary amine is tributylamine, in particular in the presence of a solvent, more particularly wherein the solvent is selected from dichloromethane, MeTHF, THF, most particularly wherein the solvent is dichloromethane as previously described, to obtain a compound of formula (III)

(III)

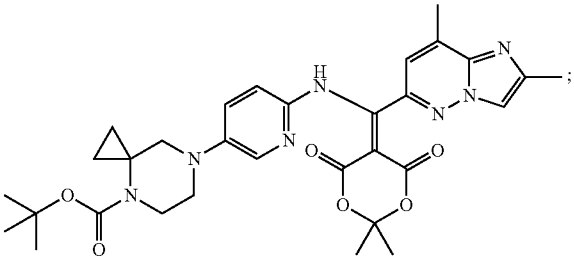

h) heating, in particular at a temperature above 70° C., in particular between 80° C. and 120° C., more particularly between 90° C. and 110° C., most particularly at 92° C.±5° C., a mixture of a compound of formula (III) in particular in the presence of a solvent, more particularly wherein the solvent is selected from isopropanol, n-propanol, t-butanol, n-butanol, isobutanol, wherein the solvent is n-propanol or n-butanol or isopropanol, in particular n-propanol as previously described to obtain a compound of formula (II)

(II)

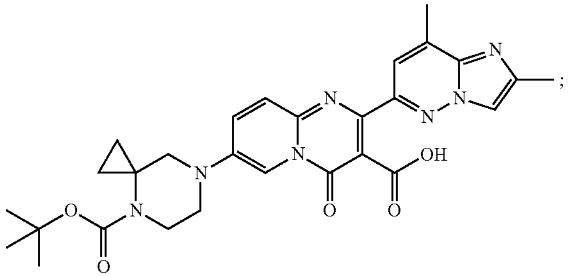

i) reacting compound of formula (II) with a strong acid (to effect the decarboxylation), in particular sulfuric acid, methanesulfonic acid, triflic acid or hydrochloric acid, in particular methanesulfonic acid, triflic acid and HCl, more particularly HCl, most particularly wherein HCl is made in situ with an alcohol and acetyl chloride, as previously described to obtain a compound of formula (I).

In another embodiment (aspect 16), the present invention provides a compound of formula (II):

(II)

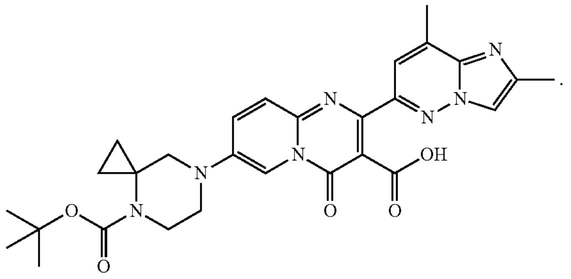

In another embodiment (aspect 17), the present invention provides a compound of formula (III):

(III)

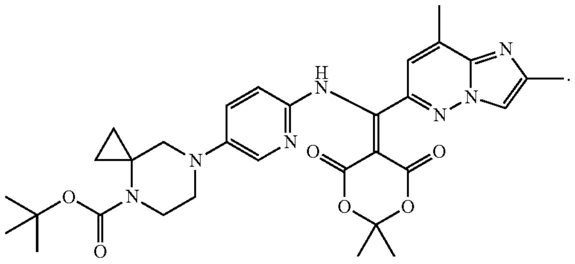

In another embodiment (aspect 18), the present invention provides a compound of formula (IV):

(IV)

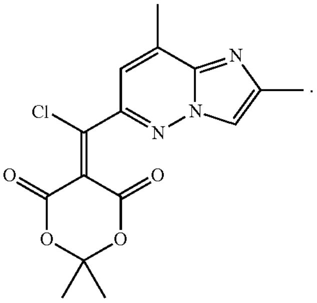

In another embodiment (aspect 19), the present invention provides a compound of formula (V) or its tautomer:

(V)

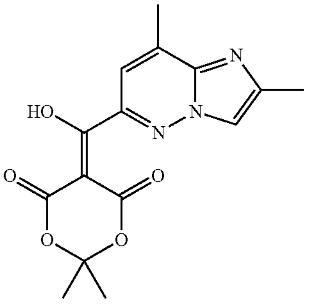

(V-tautomer)

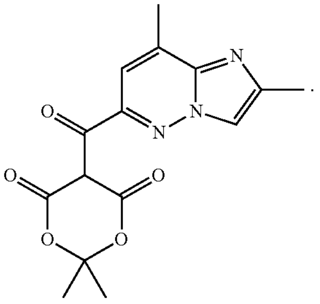

In another embodiment (aspect 20), the present invention provides a compound of formula (VI):

(VI)

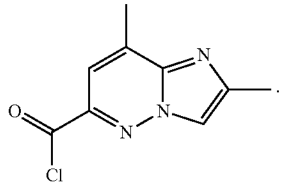

In another embodiment according to any embodiments of aspect 9 to 12 where the steps are being telescoped.

In a particular embodiment of any of the mentioned embodiment of the invention as disclosed herein step b) leading to compound formula (VIII) is optionally followed by at least a purification step, in particular wherein a purification step is an inverse crystallization. The inverse crystallization is optionally followed by a chromatography purification.

The starting materials and reagents, which do not have their synthetic route explicitly disclosed herein, are generally available from commercial sources or are readily prepared using methods well known to the person skilled in the art.

In general, the nomenclature used in this Application is based on AUTONOM™ 2000, a Beilstein Institute computerized system for the generation of IUPAC systematic nomenclature. Chemical structures shown herein were prepared using MDL ISIS™ version 2.5 SP2. Any open valency appearing on a carbon, oxygen or nitrogen atom in the structures herein indicates the presence of a hydrogen atom.

The following examples are provided for the purpose of further illustration and are not intended to limit the scope of the claimed invention.

In the present application, the following abbreviations and definitions are used: AmOH (Amzl alcohol); br (broad); BuLi (butyllithium); $CDCl_3$ (deuterated chloroform); d (doublet); DCM (Dichloromethane); DMA (Dimethylacetamide); DMAP (4-dimethylaminopyridine); DMF (Dimethylformamide); eq. (equivalent); EtOH (ethanol); g (gram); GC (gas chromatography); h (hour); HCl (hydrochloric acid); $H_2O$ (water); HPLC (High-Performance Liquid Chromatography); iPrOH (isopropanol); ISP (Isotopic Spin Population); KOH (Potassium Hydroxide); LDA (Lithium Diisopropylamide); LCMS (Liquid chromatography-mass spectrometry); M (Molar); m (multiplet); MeOH (methanol); MS (Mass Spectroscopy); mL (milliliter); NaOH (Sodium hydroxide); NMP (N-Methyl-2-Pyrrolidone); NMR (nuclear magnetic resonance); $Pd(Xantphos)Cl_2$ (Dichloro [9,9-dimethyl-4,5-bis(diphenylphosphino)-xanthene]palladium(II)); n-PrOH (n-Propanol); s (singlet); sec (second); t (triplet); t-Bu Brett Phos (2-(Di-tert-butylphosphino)-2',4',6'-triisopropyl-3,6-dimethoxy-1,1'-biphenyl); THF (tetrahydrofuran): 2-Me-THF (2-Methyltetrahydrofuran).

EXAMPLE 1

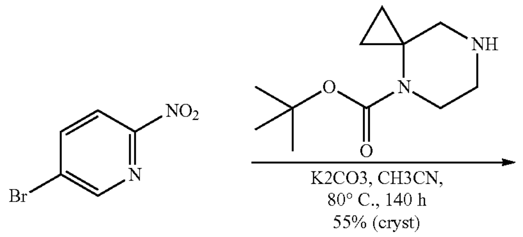

-continued

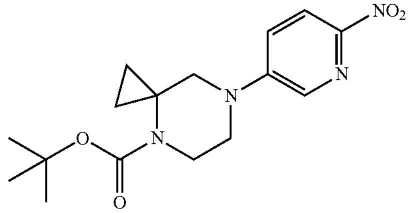

5-bromo-2-nitropyridine (800 g, 3.94 mol, Eq: 1.00) and tert-butyl 4,7-diazaspiro[2.5]octane-4-carboxylate (944 g, 4.45 mol, Eq: 1.13) were charge in the reactor followed by Acetonitrile (1.57 kg, 2 l, Eq: -). A suspension of anhydrous potassium carbonate (1.5 kg, 10.9 mol, Eq: 2.75) in Acetonitrile (2.36 kg, 3 l, Eq: -) was added. The suspension was stirred and heated to 80° C. over 3 days.

The resulting orange suspension was cooled to 50° C. and Water (12 kg, 12 L, Eq: -) in ca min (solution). A suspension was rapidly obtained and was cooled to 20° C. After 1 h at 20° C., the suspension was filtered. The filter cake was washed sequentially with water (3 kg, 3 L, Eq: -), Ethanol (1.58 kg, 2 l, Eq: -) and MTBE (740 g, 1 L, Eq: -). The filter cake was transferred to a reactor together with ethanol (7.1 kg, 91, Eq: -) and toluene (865 g, 1 L, Eq: -). The suspension was heated to 60° C. and stirred for 1 h and cooled to 20° C. over 2 h. The suspension was stirred overnight and filtered. The filter cake was washed with Ethanol (800 mL) and was dried at 50° C./<10 mbar over weekend to give 737 g of product (99.5a % purity by HPLC). LCMS: 335.17 (M+1).

EXAMPLE 2

Tert-butyl 7-(6-aminopyridin-3-yl)-4,7-diazaspiro [2.5]octane-4-carboxylate

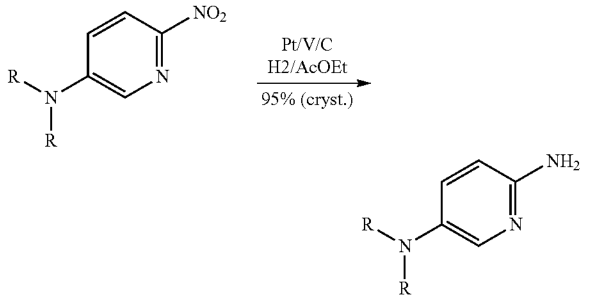

230 g tert-butyl 7-(6-nitropyridin-3-yl)-4,7-diazaspiro [2.5]octane-4-carboxylate-tert-butyl 7-(6-nitropyridin-3-yl)-4,7-diazaspiro[2.5]octane-4-carboxylate (1 eq., 2.09 mol) was hydrogenated in AcOEt (7 L, 6.3 kg) with wet 1% Pt/C+2% Vanadium (0.38% Pt, 0.065 mol %) at RT under 1 bar H2. After reaction completion, the reactor was evacuated and the reaction mixture was filtered. The reaction was repeated twice (total ca 700 g SM)) and the combined product were concentrated to ca 1 L volume. Heptane (3 L) were added and the mixture was solvent exchanged to heptane under constant volume. The resulting suspension was diluted with heptane (1 L) and filtered. The filter cake was washed with heptane and dried at 50° C./<10 mbar until constant weight to give: 610 g of the title product (>99.5 a % purity by LC).

EXAMPLE 3

6-chloro-2,8-dimethylimidazo[1,2-b]pyridazine

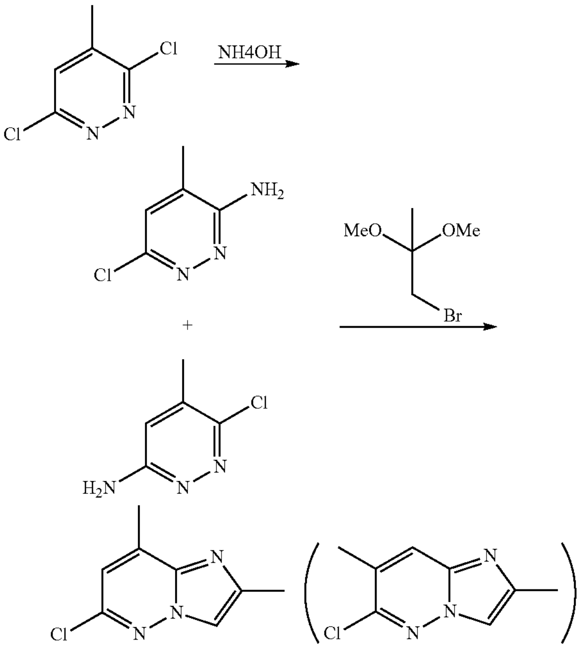

3,6-dichloro-4-methylpyridazine (200 g, 1 eq., 1.23 mol) and 25% aqueous NH4OH solution (1.8 kg, 2 L) were charged in an autoclave. The reaction mixture was heated to 100° C. for 18 h (ca 7 bar pressure) and cooled to RT. The suspension was transferred to another reactor. The autoclave was washed with water (1 L). The combined suspension was stirred overnight at RT and was filtered. The filter cake was washed with cold (0-5° C.) water (1 L) and dried at 50° C./<10 mbar.

This reaction was repeated 3 times to deliver a total of ca 334 g of the aminochloropyridazine intermediate as a mixture of isomers.

The crude intermediate product (384 g) and pyridinium p-toluenesulfonate (43 g, 171 mmol, Eq: 0.0736) were charged in the a reactor followed by 2-Propanol (1.96 kg, 2.5 l, Eq: -). The resulting suspension was heated to 80° C. and 1-bromo-2,2-dimethoxypropane (521 g, 385 ml, 2.79 mol, Eq: 1.20) was added over 25 min. The reaction mixture was stirred overnight and was cooled to RT. A 1M aqueous NaOH solution (3.78 kg, 2.8 l, 2.8 mol, Eq: 1.2) was added over 30 min at RT. The suspension was partially concentrated at ca 60° C. under reduced pressure (ca 3 L distilled) during which a solution then again a suspension was obtained. The suspension was cooled to ca 8° C. (Tj 5° C.) over 3 h. After stirring overnight, water (3.00 kg, 3 l) was added. After stirring for 1 h, the suspension was filtered. The filter cake was washed with water (2.00 kg, 21) and dried at 50° C. under reduced pressure to give 305 g of product as a mixture of isomers. The crude product was digested in ca 1.5 L of AcOEt. The suspension was filtered and the filter cake was discarded (contains mainly the undesired isomer). The filtrate was concentrated and purified by chromatography (SiO2/AcOEt) to give 128 g of product (>97a % purity by LC, undesired isomer not detected) LC-MS: 182 (M+1).

EXAMPLE 4

2,8-dimethylimidazo[1,2-b]pyridazine-6-carboxylic acid

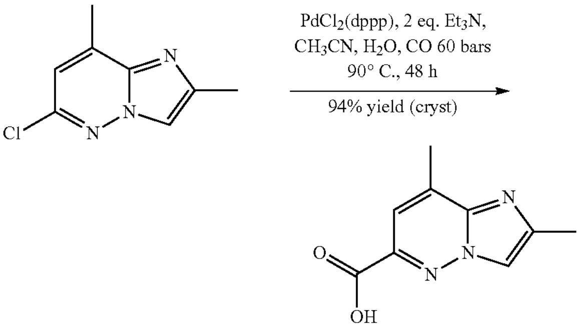

6-chloro-2,8-dimethylimidazo[1,2-b]pyridazine (400 g, 1 eq., 2.2 mol) was carbonylated in a mixutre of acetonitrile (3.2 L, 2.52 kg) and water (0.8 L, 0.8 kg) with PdCl2(dppp) (13 g, 0.01 eq.), triehtylamine (448 g, 617 ml, 2 eq.) and CO (60 bar) at 90° C. for 48 h. After completion of the reaction, the reactor was cooled, evacuated and the reaction mixture was filtered. The filtrate was concentrated under reduced pressure/60° C. to 2.4 L. The solution was azeotroped at constant volume. To the resulting suspension was cooled to RT, dichloromethane (8 L) was added, followed by 5-6N HCl in iPrOH (400 g, 440 mL, 1.1 eq). The suspension was further stirred for 1 h and was filtered. The filter cake was washed with dichloromethane (5 L) and was dried at 50° C./<10 mabr until constant weight to give 397 g of the title product (99.8 a % LC, 0.5% KFT). LCMS: 192.07 (M+1)

EXAMPLE 5

7-(4-(tertbutoxycarbonyl)-4,7-diazaspiro[2.5]octan-7-yl)-2-(2,8-dimethylimidazo[1,2-b]pyridazin-6-yl)-4-oxo-4H-pyrido[1,2-a]pyrimidine-3-carboxylic acid

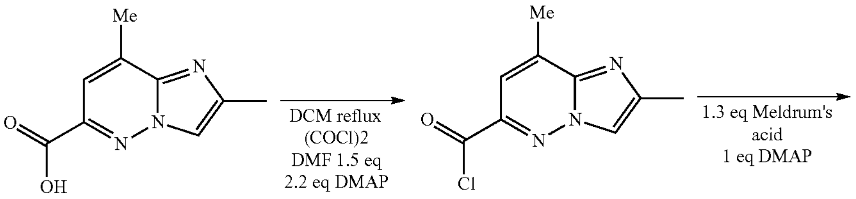

INT-1

-continued

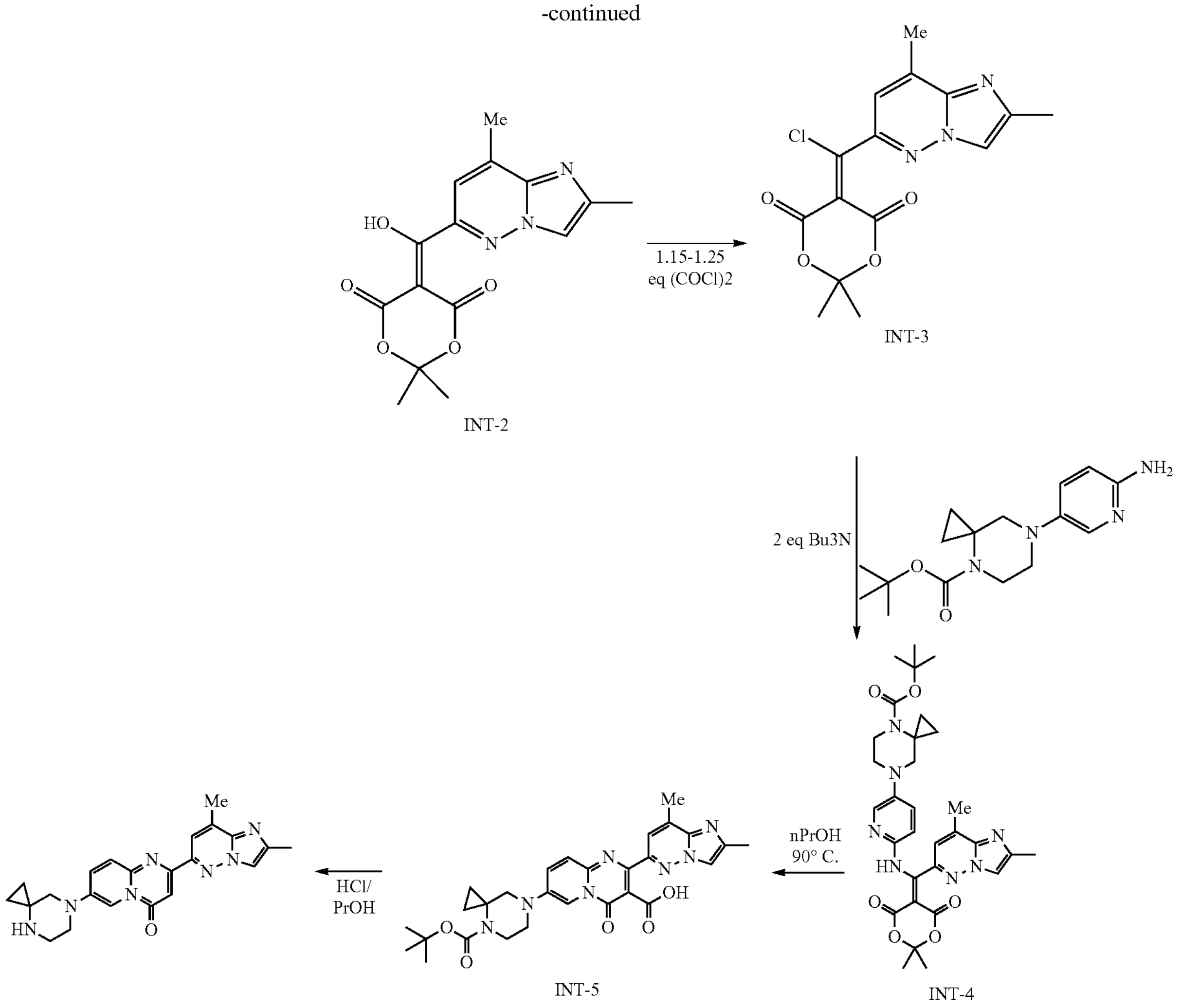

2,8-dimethylimidazo[1,2-b]pyridazine-6-carboxylic acid (300 g, 1.57 mol, Eq: 1) and DMAP (422 g, 3.45 mol, Eq: 2.2) were charged in the reactor followed by DCM (7.92 kg, 6 l, Eq: -) and DMF (132 g, 140 ml, 1.81 mol, Eq: 1.15). The mixture was heated to 40° C. during which a solution was obtained. A solution of oxalyl chloride (203 g, 138 ml, 1.57 mol, Eq: 1) in DCM (792 g, 0.6 l Eq: -) was added dropwise in ca 45 min. After completion of the reaction (to give INT-1, <30 min, IPC by LC after derivatization), the resulting suspension was cooled to RT and added to a solution of 2,2-dimethyl-1,3-dioxane-4,6-dione (Meldrum's acid) (294 g, 2.04 mol, Eq: 1.3) and DMAP (192 g, 1.57 mol, Eq: 1) in DCM (5.28 kg, 4 l, Eq: -) at RT. After 1 h reaction (to give INT-2, IPC check), a solution of oxalyl chloride (184 g, 125 ml, 1.42 mol, Eq: 0.905) in DCM (330 g, 250 ml, Eq: -) was added over 30 min. Additional oxalyl chloride was added in portion ("titration") until the amount of intermediate INT-2 was <2a % (total amount of oxalylchlorid: 68 g/0.34 eq). After completion of the deoxychlorination (to give INT-3), a solution of tert-butyl 7-(6-aminopyridin-3-yl)-4,7-diazaspiro[2.5]octane-4-carboxylate (430 g, 1.41 mol, Eq: 0.9) and tributylamin (594 g, 764 ml, 3.14 mol, Eq: 2) in DCM (1.58 kg, 1.2 l, Eq: -) was added over 20 min. The reaction mixture was stirred overnight and concentrated (to give crude INT-4). Propanol (3 L) was added and the mixutre was concentrated. The last 2 operations were repeated. Propanol (6 L) was added and the reaction mixture was heated to reflux overnight to effect the cyclization leading to a crude mixture containing INT-5.

In a separate reactor, acetylchlorid (829 g, 750 mL, 10.5 mol, Eq: 7.16) was added to 1-propanol (2.56 kg, 3.2 L, Eq: -) keeping the temperature between 10-20° C. After completion of the reaction the HCl solution in propanol was heated to 60° C. and the crude solution of INT-5 prepared before (heated to 90° C. to get a solution then cooled down to 60° C.) was added dropwise over 25 min at 60° C. (this effects Boc-deprotection and ca 20% decarboxylation). The resulting reaction mixture was heated to reflux (ca 92° C. down to 89° C. over time) overnight to complete the decarboxylation. The reaction mixture was cooled to RT and filtered. The filter cake was washed with propanol. The filter cake was dissolved in water (3 L) and ethanol (3 L) was added. A 32% aqueous NaOH solution (234 g, 173 mL, 1.87 mol, Eq: 1.28) was added to adjust the pH to 13 during which the product crystallized. The suspension was heated to ca 50° C. for 24 h. The suspension was cooled to RT for 15 h and was filtered. The filter cake was washed with a 1:2 ethanol/water mixutre (2 L). The filter cake was dried at 50° C. under vacuum with a water saturated atmosphere to give 384 g of product as a trihydrate (98a % purity by LC, water: 12.4% m/m).

What is claimed is:

1. A process for the preparation of a compound of formula (I) or the HCl salt thereof:

(I)

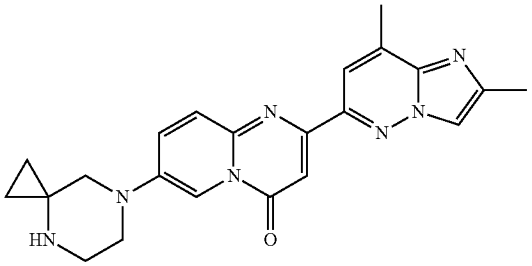

which comprises reacting compound of formula (II):

(II)

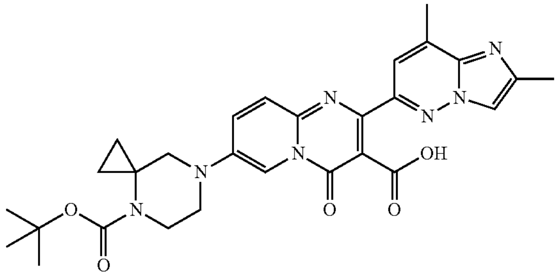

;

with a strong acid.

2. The process according claim 1, wherein the strong acid is HCl, and the HCl is made in situ with n-propanol and acetyl chloride.

3. The process according to claim 1, which further comprises the preparation of a compound of formula (II)

(II)

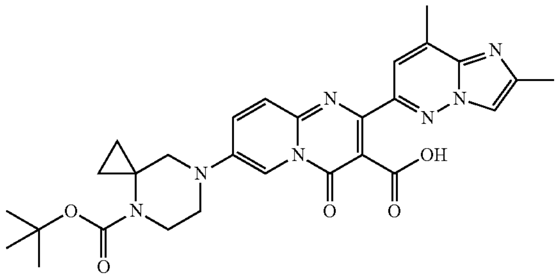

;

comprising heating a compound of formula (III)

(III)

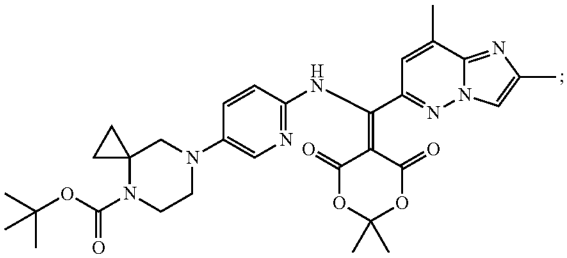

;

in the presence of a solvent.

4. The process according claim 3, which further comprises the preparation of a compound of formula (III)

(III)

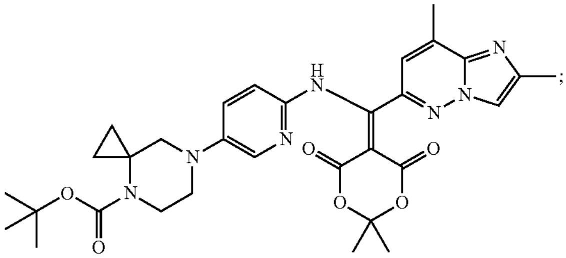

;

comprising reacting a compound of formula (IV)

(IV)

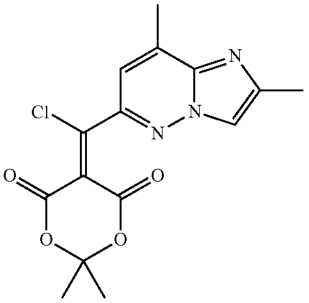

with a compound of formula (IVa):

(IVa)

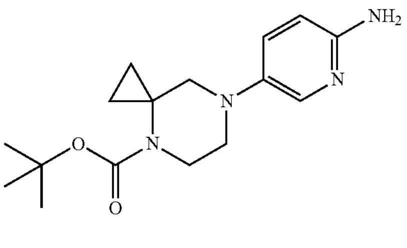

in the presence of a tertiary amine and a solvent.

5. The process according to claim 4, which further comprises the preparation of a compound of formula (IV)

(IV)

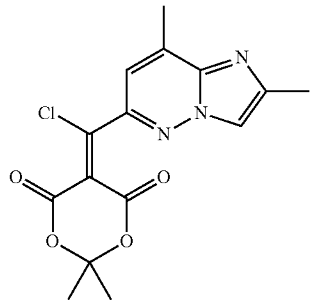

comprising reacting a compound of formula (V) or its tautomer (V)

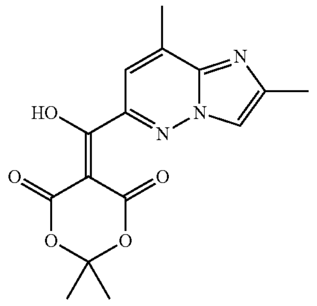

(V-tautomer)

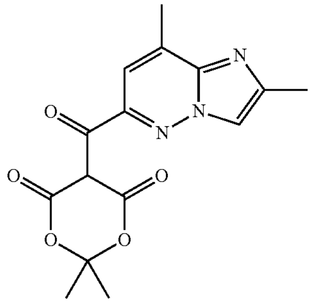

with oxalyl chloride in the presence of a solvent.

6. The process according to claim 5, which further comprises the preparation of a compound of formula (V)

(V)

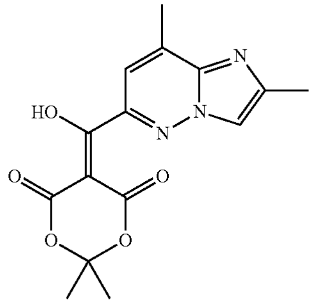

which comprises reacting a compound of formula (VI)

(VI)

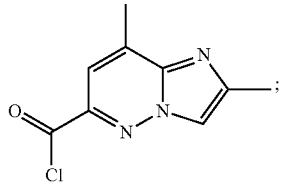

;

with 2,2-dimethyl-1,3-dioxane-4,6-dione in the presence of a solvent and DMAP.

7. The process according to claim 6, which further comprises the preparation of a compound of formula (VI)

(VI)

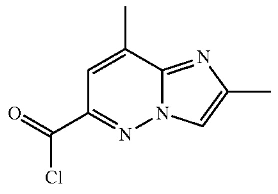

which comprises reacting a compound of formula (VII)

(VII)

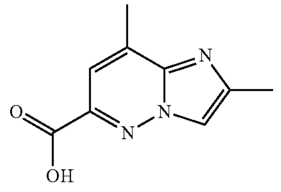

with oxalyl chloride, in particular in presence of a solvent and DMAP.

8. The process according to claim 7, which further comprises the preparation of a compound of formula (VII)

(VII)

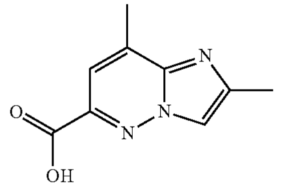

which comprises reacting a compound of formula (VIII)

(VIII)

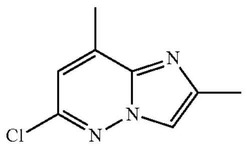

with carbon monoxide in the presence of a catalyst a base, water, and a solvent.

9. The process according to claim 8, which further comprises the preparation of a compound of formula (VIII)

(VIII)

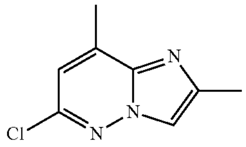

which comprises:

a) Reacting a compound of formula (X)

(X)

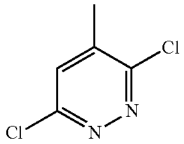

with $NH_4OH$ to obtain a compound of formula (IXa), and b) reacting the compound of formula (IXa)

(IXa)

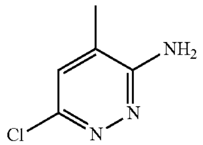

with 1-bromo-2,2-dimethoxypropane, in the presence of pyridinium p-toluenesulfonate, to obtain the compound of formula (VIII).

10. A compound of formulae (II) or (III):

(II)

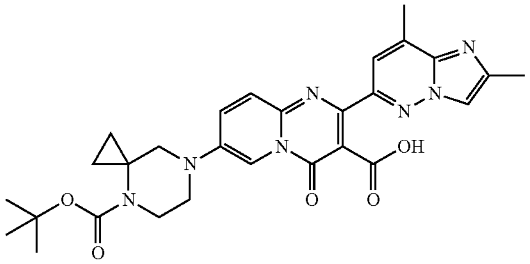

or

-continued (III)

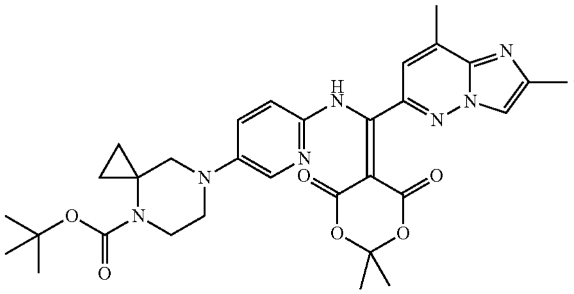

11. The process of claim 3, wherein the compound of formula (III) is heated at a temperature between 80° C. and 120° C. in the presence of a solvent selected from the group consisting of isopropanol, n-propanol, t-butanol, n-butanol, and isobutanol.

12. The process of claim 4, wherein the tertiary amine is selected from the group consisting of triethylamine, tripropylamine, diisopropylethylamine, and tributylamine; and the solvent is selected from the group consisting of dichloromethane, MeTHF and THF.

13. The process of claim 5, wherein the solvent is selected from the group consisting of dichloromethane, 2-MeTHF, THF, DMF, and NMP.

14. The process of claim 6, wherein the solvent is selected from the group consisting of dichloromethane, 2-MeTHF, THF, DMF, and NMP; and the 2,2-dimethyl-1,3-dioxane-4,6-dione is added in the presence of DMAP wherein the DMAP is present 2.0 to 2.5 equivalents with respect to the theoretical amount of compound of formula (VI).

15. The process of claim 7, wherein the solvent is selected from the group consisting of dichloromethane, 2-MeTHF, THF, DMF, and NMP; and DMAP is present at 1.5 to 4.0 equivalents with respect to the theoretical amount of compound of formula (VII).

16. The process of claim 8, wherein the catalyst is selected from the group consisting of $Pd(PPh_3)_4$, $Pd(PPh_3)_2Cl_2$, $PdCl_2(dppf)$, $PdCl_2(dppf)\cdot CH_2Cl_2$, and $PdCl_2(dppp)$; the base is a tertiary amine; and the solvent is selected from the group consisting of MeOH, EtOH, iPrOH, AmOH, n-PrOH, DMF, DMA, Toluene, TH, and 2-Me-THF.

* * * * *